United States Patent [19]

Bacon et al.

[11] Patent Number: 4,471,189

[45] Date of Patent: Sep. 11, 1984

[54] SEALED, MODULAR KEYBOARD PROVIDING A TACTILE FEEL

[75] Inventors: Rémy Bacon, Dignac; Gérard Juery, Ruelle, both of France

[73] Assignee: La Telemecanique Electrique, France

[21] Appl. No.: 413,585

[22] Filed: Aug. 31, 1982

[30] Foreign Application Priority Data

Sep. 1, 1981 [FR] France ............................... 81 16623

[51] Int. Cl.³ ............................................... A01H 3/12

[52] U.S. Cl. ............................... 200/159 B; 200/314; 200/340; 200/5 A

[58] Field of Search .................... 200/159 B, 314, 302, 200/292, 317, 340, 5 A, 330, 310

[56] References Cited

U.S. PATENT DOCUMENTS

| | | | |
|---|---|---|---|
| 3,133,170 | 5/1964 | Nanninga | 200/159 B |
| 3,749,859 | 7/1973 | Webb et al. | 200/159 B X |
| 3,849,621 | 11/1974 | Habecker | 200/310 |
| 3,860,771 | 1/1975 | Lynn et al. | 200/5 A |
| 3,999,025 | 12/1976 | Sims, Jr. | 200/159 B |
| 4,004,120 | 1/1977 | Lee | 200/310 |
| 4,056,701 | 11/1977 | Weber | 200/314 |
| 4,066,850 | 1/1978 | Heys, Jr. | 200/5 A |
| 4,131,777 | 12/1978 | Bailey et al. | 200/314 X |
| 4,288,672 | 9/1981 | Puccini | 200/314 |
| 4,331,851 | 5/1982 | Johnson | 200/159 B |

FOREIGN PATENT DOCUMENTS

| | | | |
|---|---|---|---|
| 2037079 | 7/1980 | United Kingdom | 200/159 B |

*Primary Examiner*—Charles E. Phillips
*Assistant Examiner*—Ernest Cusick
*Attorney, Agent, or Firm*—William A. Drucker

[57] ABSTRACT

The keyboard comprises a printed circuit (4) serving both as an electrical connection means and as a supporting means for a modular frame (3) including a plurality of square-shaped housings (30) defined by walls (31) and arranged in rows and columns, either contact modules (7) or signal-lamp modules fitted on said printed circuit in said housings, a resilient, sealed diaphragm (1) secured to said frame, keys cooperating with said contact modules through the portions of said keys which face outwardly from said diaphragm and are actuated by an operator finger, and means (105, FIG. 5; 9, FIG. 2) by which a tactile feel can be provided through a snapping, movement.

9 Claims, 13 Drawing Figures

SEALED, MODULAR KEYBOARD PROVIDING A TACTILE FEEL

BACKGROUND OF THE INVENTION

The invention relates to a modular, sealed keyboard providing a tactile feeling.

It is particularly applicable to short-stroke keyboards for digital control machines, programmable automatons, typewriters and word processing machines.

THE PRIOR ART

It is known in manufacture of sealed, thin and low-cost keyboards, to apply by silk-screening an electrically conducting ink onto one side of a plastic sheet, the other side of which bears the written material corresponding to the types, to apply again electrically conducting ink onto one side of another flexible plastic sheet, to bond both sheets together so that the respective ink-coated sides are disposed in a face-to-face relationship while being spaced from each other by a thin air gap of a few tenths of a millimeter. There is thus obtained a thin and sealed keyboard which can be easily cleaned, but the reliability of which is not sufficient for use with industrial products.

In addition, the above type of keyboard has the major drawback that it does not have a stroke such as the operator can appreciate without a display means, i.e. by mere tactile sensing, whether his operation has been taken into account by the keyboard-connected machine.

There are also known reliable and strong keyboards of the typewriter kind having depressable keys with long strokes of about 4 mm such that the operator can appreciate without any display means that a particular key was operated. However, such keyboards, due to their long stroke, are not sealed and their maintenance is not easy.

OBJECT OF THE INVENTION

The invention has all the advantages of the above various keyboards while overcoming their respective drawbacks.

The invention provides a keyboard which is reliable, sealed from the environment, easy to maintain, strong, modular and of low-cost.

SUMMARY OF THE INVENTION

In accordance with the invention, the keyboard comprises a printed circuit board serving both as an electrical connection means and as a supporting means for a modular frame in which are provided a plurality of square-shaped housings defined by walls or partitions and arranged in rows and columns, contact modules or signal lamp modules mounted on the printed circuit board in the frame housings, a resilient, sealed diaphragm secured to said frame, keys cooperating with said contact modules through portions of said keys disposed above said diaphragm which are operated with a finger and means for achieving a tactile feel by snapping movement.

BRIEF DESCRIPTION OF THE DRAWINGS

Other features and advantages of the invention will become apparent from the detailed description hereinbelow.

In the appended drawings.

DESCRIPTION OF THE PREFERRED EMBODIMENT

Figure 1:
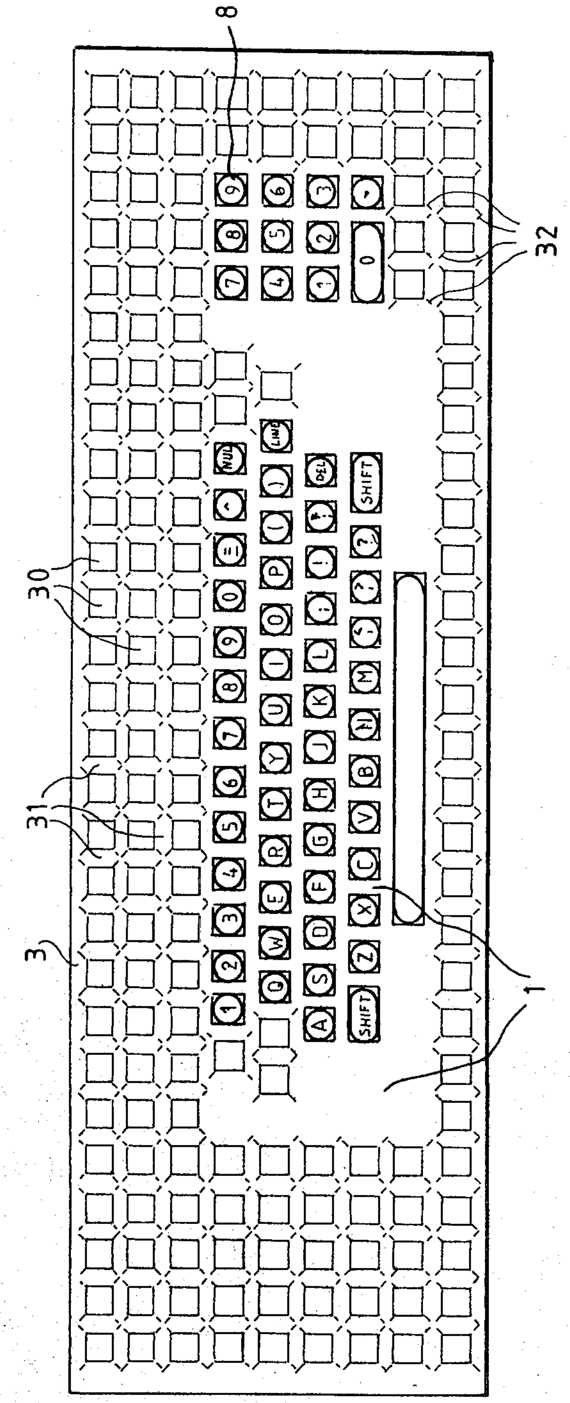
FIG. 1 shows a top view of a keyboard supported, through a diaphragm on a modular frame associated therewith.

FIG. 1 shows a set of keys 8 supported on a diaphragm a part of which has been broken away to make visible a frame or spacer 3 on which is supported the key diaphragm assembly. The modular spacer 3 is a molding which comprises a plurality of housings 30 arranged in rows and columns. Said plurality of square-shaped housings are defined by partition walls in which pre-cuts are provided so that the size of a particular aperture can be changed and housings having a length which corresponds to a plurality of modules can be obtained. In these housings are disposed, either contact modules or signal-lamp modules, depending upon the kind of keyboard to be provided, and with said contact modules cooperate square-shaped keys bearing the alphanumerics or other signs corresponding to the desired keyboard. Depending upon the kind of desired keyboard, either the whole or part of the modular spacer will be used.

As disclosed hereinlater, by using such a spacer in combination with modular components forming a keyboard, keyboards which can easily be adapted to particular needs can be achieved.

Figure 2:
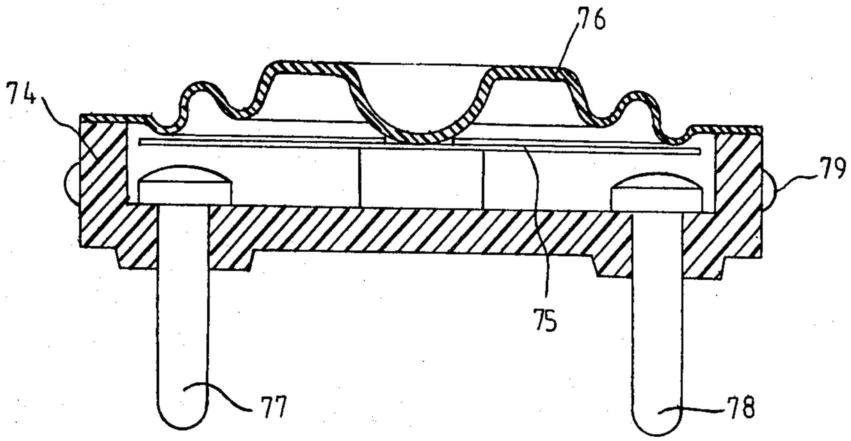
FIG. 2 is a cross-sectional view of a contact module.
Figure 3:
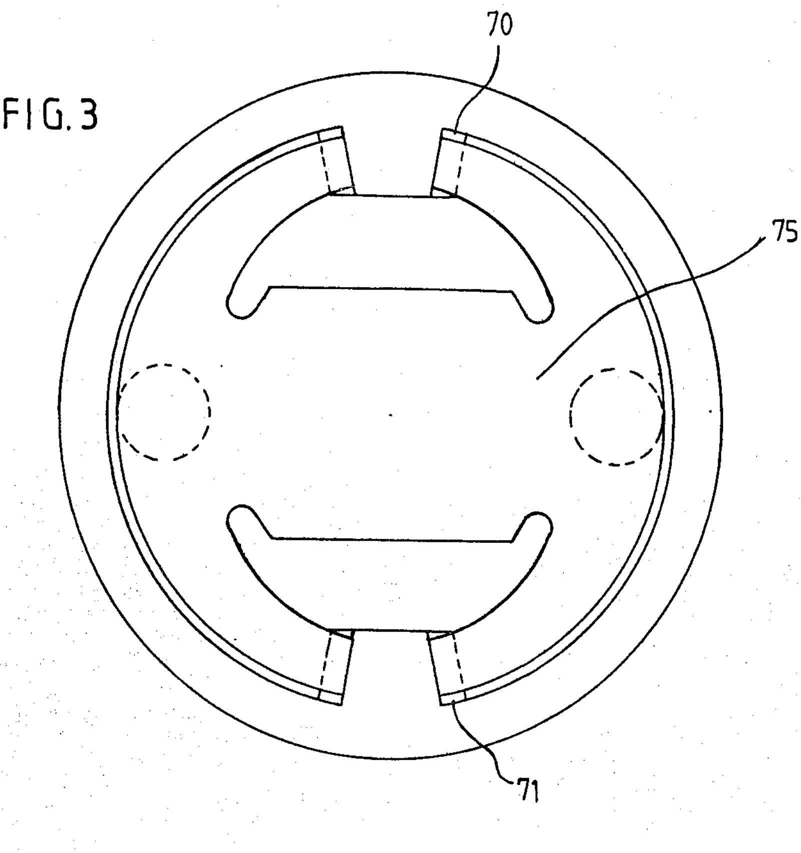
FIG. 3 is a top view of the said contact module.
Figure 4:
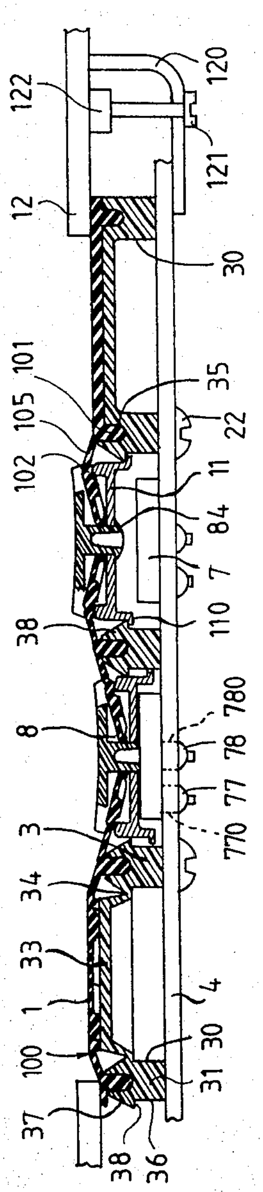
FIG. 4 is a cross-sectional view of a first embodiment of the keyboard.

FIGS. 2 and 3 illustrate a contact module for use in the keyboard of FIG. 1 or 4, including a circular-shaped polycarbonate casing 74 through the bottom of which are provided a pair of holes for allowing passage of a pair of pins 77,78 made of an electrically conducting material and having contact heads. The casing bottom also has a pair of bosses 70,71 (FIG. 3). A contact strip 75 made of a thin sheet of an electrically conducting material is accomodated in the casing, in supporting engagement with bosses 70,71 and pin 77, so that, in the inoperative position, no electrical connection is provided between pins 77 and 78, such a connection being however provided in the operative position. A thin sealed film of polycarbonate material forming a diaphragm 76 is either adhesively bonded or welded to casing 74. The pins 77, 78 pass through holes 770, 780 of the printed circuit board. (FIG. 4) and the contact module is secured to the printed circuit board by welds which also provide electrical connection between the pins 77, 78 and the printed circuit board.

Such a type of contact module, for use with keyboards of the kind of FIG. 4 has the advantage not to provide a tactile feel resulting from occurrence of a "tough" point. Such a contact module thus prevents superimposition of a tactile feel caused by the module onto the tactile feel caused by boss 105 of FIG. 4.

Casing 74 is provided with a circularly extending rib 79 in its peripheral portion.

In use, when the operator depresses a key of the keyboard, diaphragm 1 becomes deformed while opposing an increasing resistant force until some limit, at which it snaps into a position in which it engages the diaphragm 76 of the contact module and brings contact strip 75 into engagement with pins 77 and 78. Such snapping movement of the strip provides a tactile feel to the operator. Diaphragm 1 provides sealed condition of the keyboard. The keyboard will be mounted against the inner side of a casing 12 (FIG. 4) of the apparatus associated therewith, in such a way that the casing and the keyboard will be sealingly connected through tightening of diaphragm 1.

Figure 5:
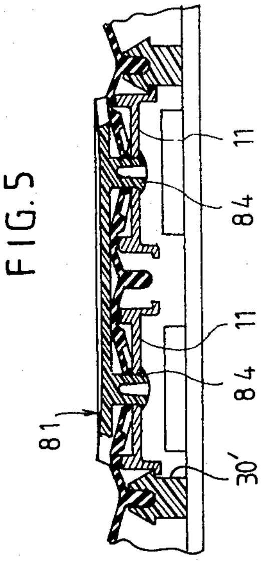
FIG. 5 is a cross-sectional view of a double key.

FIG. 5 illustrates a sealed, modular keyboard having a support consisting of a printed circuit board on which are mounted contact modules 7, at the locations corresponding to the housings of a modular spacer or frame 3, which is secured to said printed circuit board, e.g. by means of screws 22. Modular spacer 3 may also be secured to printed circuit board 4 by crimping or any other fastening means. Modular spacer or grid 3 includes, partition walls 31 separating the housings from the precuts 32, which allows a number of walls to be removed to provide housings having dimensions adapted to the keys. Covers 33 are connected to the partition walls defining by a thin web 34, whereby, by pressing the cover, the cover can be removed from the spacer and an opening can be obtained at the selected location to place a key 30. The spacer walls have a planar lower surface which engages the printed circuit board 4, an upper surface in whih a longitudinally extending groove is provided, and a pair of side surfaces each having a vertical portion 36 and an inclined portion 37 defining a shoulder 38 with said vertical portion 36.

The cover surfaces facing outwardly from the housings extend in a plane parallel to the plane in which extend said upper surfaces of the walls.

A diaphragm 1, made of a polyurethane or any other resilient and sealed material which is easily moldable, has bosses 100 in the shape of truncated pyramids with a square base, the upper base of which either cooperates with a key, or is supported on the upper surface of the associated cover in case where there is no key, and the lower base of which is secured to the spacer by longitudinal and transverse ribs 101 which are secured in grooves 35 of spacer 3 by adhesive bonding, crimping, welding or any other suitable means.

Figure 11:
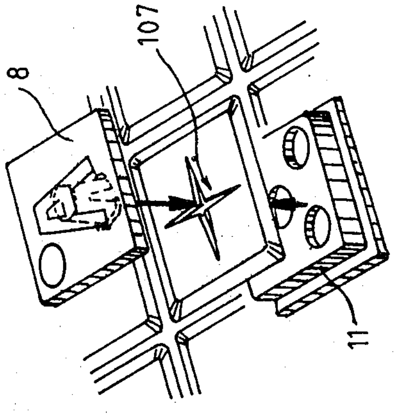
FIG. 11 is a perspective view of a first mode of assembly of the key.
Figure 10:
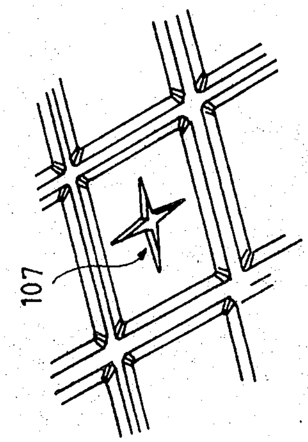
FIG. 10 is a perspective view of the sealed diaphragm.

The upper base of the diaphragm boss includes a protruding rim 102 sealingly connecting the base with the key 8. Key 8 is mounted on said upper base after a cross-shaped notch or slot has been cut through the diaphragm, as shown in FIGS. 10 and 11, for allowing passage of head 84 of key 8 snapping into connecting member 11. Member 11 includes a flange 110 for limiting displacement therefore by abutting against shoulder 38. Said flange also cooperates with the vertical portions 36 of the walls which enclose the housing, so as to form a guide means for the key while the latter is moving in the vertical direction.

Thus, by removing the housing covers where keys are to be inserted and by fitting the desired keys at the desired locations, there is obtained a sealed keyboard which, starting from modular components, can be provided with the desired key arrangement and number.

The sealed engagement between the keyboard and casing 12 of the apparatus using the keyboard is obtained by tightening the diaphragm against casing 12, e.g. by means of a device, such as shown in FIG. 4 including a nut 122 welded to the casing, a flange 120 and a screw 121.

In use, when a key is depressed, the side portions of the boss are squeezed until the diaphragm abruptly assumes the shape of an inverted pyramid as shown in FIG. 5, thus generating a tactile feel. In this depressed position the key establishes electrical connection between pins 77 and 78. As soon as the key is released, the diaphragm recovers its original shape. Where there is no key, cover 33 provides support to the diaphragm boss and prevents the diaphragm from being collapsed.

FIG. 5 illustrates how a multiple key, e.g. a double key, is made and fitted in place. The double key 81 has twice the length of a single key plus the distance between two adjacent single keys of the type illustrated in FIG. 4. The double key has a pair of snapping heads 84 which are mounted, through a pair of connecting members 11, onto diaphragm 1 in turn secured to spacer 3. An intermediate wall of diaphragm 1 has been removed where the double key is to be mounted.

Figure 6:
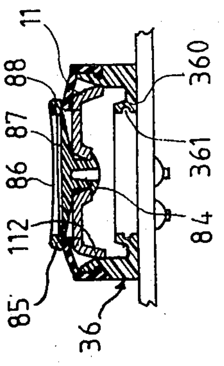
FIG. 6 is a cross-sectional view of a single key using another embodiment of a modular and sealed diaphragm.
Figure 7:
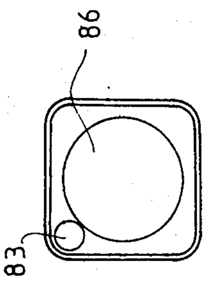
FIG. 7 is a top view of a key having a signal-lamp.

In the embodiment of FIG. 6, the walls 31 of spacer 3 instead of having a shoulder 38 as in the embodiment of FIG. 4 have, on their vertical portions 36, an extension 360 defining a circular opening through which a contact module can be secured by snapping of rib 79 (FIG. 2) into a matching groove 361. Connecting member 11, instead of having a flange as in the embodiment of FIG. 4, has a guiding surface 112 and is snap-fastened to a label-holding key. The latter consists of a body 85 comprising a label cover 86 made of a transparent material and a label 87 in a housing 88.

Figure 12:
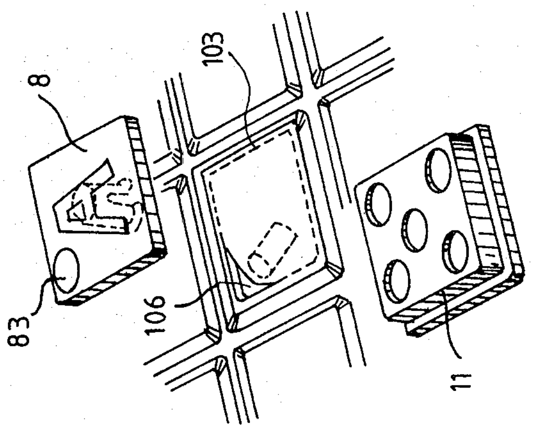
FIG. 12 is a perspective view of a second mode of assembly of the key.
Figure 13:
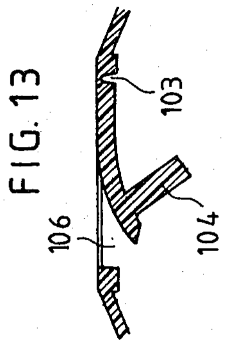
FIG. 13 is a cross-sectional view of a second embodiment of the diaphragm as used in the second mode of assembly of the key.

The key body 85 and the connecting member 11, once assembled together, clamp there-between, so that sealing engagement is provided between the key and diaphragm, a protruding rim 102 which is formed around an opening provided through the diaphragm in the manner as shown in FIGS. 12 and 13. A tongue 104 allows removal of a patch of diaphragm previously cut along score line 103 defining a square shape and to obtain an opening 106 through which a key can be inserted as shown in FIG. 6.

Figure 8:
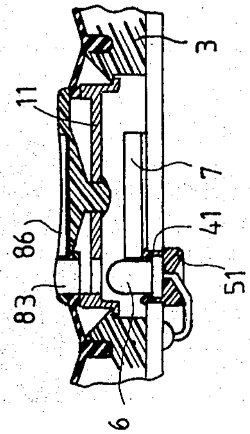
FIG. 8 is diagonal sectional view of the key of FIG. 7.

FIG. 8 shows a top view of a square-shaped key having in one corner thereof a clear circular window 83 for a signal-lamp and a circular-shaped label cover 86 matching with finger contour.

FIG. 8 shows a diagonal sectional view of the key including said signal-lamp in its position as mounted on the keyboard in a housing including, in addition to the contact module 7, a support 51 for a light-emitting diode 6 fitted in an opening 41 provided in the printed circuit board. The connecting member 11 in the housing is provided with a small window 111 opposite the diode and the clear port-hole on the key.

Figure 9:
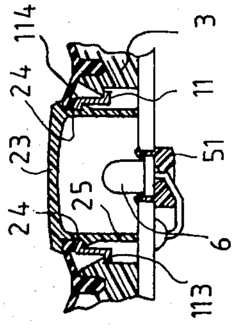
FIG. 9 is a cross-sectional view of a fixed signal-lamp.

FIG. 9 illustrates how a fixed signal-lamp is inserted through an opening provided for a key in which a support for a lightemitting diode 6 has been fitted on the printed circuit board. A viewing cap made of a transparent material and having a shape matching with the cut-out portion of the diaphragm has on its side surfaces 25 a groove 24 in which the protruding rim 102 of the diaphragm is clamped by an inner flange 114 provided on the connecting member which snaps into the cap. An outer flange 113 and said side surfaces 25 prevent any movement of the cap with respect to the spacer. Thus, through such modular components, spacers and diaphragms having predetermined dimensions, sealed keyboards having or not signal-lamps and adapted to all types of uses can be made as required. It should be clear that, in the above disclosed embodiments, the construction can be stiffened by fitting an angle bar 13 on the printed circuit board.

It should be understood that various changes can be made in the above described and illustrated embodiments without departing from the scope of the invention.

We claim:

1. A keyboard comprising:

a printed circuit board;

a switch having a movable contact member adapted for electrical coupling with the printed circuit board;

a generally plane insulating rigid frame having outer and inner faces and forming on the inner face thereof at least one housing having walls, said walls having a free edge surface portion and an inner surface portion, the said inner surface portion being substantially at right angles to the frame and having retaining means and means for securing said frame on to said printed circuit board with the said movable contact member lodged in said housing;

a deformable diaphragm overlaying said frame on the outer face thereof and having at least one surface portion facing said housing and means for securing said surface portion of the diaphragm to the said free edge surface portion, said surface portion of the diaphragm having an aperture and being shaped for snapping displacement with tactile feel;

at least one key member having outer and inner parts and a further part passing through said aperture and secured to said surface portion of the diaphragm, said further part coupling the outer and inner parts together, the outer part being shaped for finger activation and the inner part having a peripheral surface portion shaped for sliding along the said inner surface portion of the wall and having abutting means cooperating with the said retaining means, the inner part having a further surface portion which engages the movable contact member when the outer part has been pushed to an operating position in which the said surface portion of the diaphragm has effected the said snapping displacement.

2. A keyboard as claimed in claim 1, wherein the said surface portion of the diaphragm has a frusto-pyramidal shape.

3. A keyboard as claimed in claim 1, wherein the said switch comprises at least one modular unit having a casing lodged in said housing and conducting pins which form stationary contacts of the switch and cooperate with the said movable contact member and the said printed circuit board has holes in which said conducting pins are secured.

4. A keyboard according to claim 3, wherein the casing of said modular unit has a bottom which is provided with a pair of bosses and said conducting pins extend through said bottom, said movable contact member comprising a metal contact strip which is supported by said bosses and a further diaphragm forming a cover for said casing.

5. A keyboard as claimed in claim 1, wherein said means for securing the diaphragm to the free edge surface portion essentially consist of a groove provided in the said free edge surface portion of a rib and provided in the said surface portion of the diaphragm, said rib being engaged in said groove, said abutting means essentially consist of a flange and said retaining means essentially consist of a shoulder arranged for stopping said flange.

6. A keyboard according to claim 1, wherein the said inner part of the key member has a protruding surface and said deformable diaphragm has a protruding rim, the said protruding rim being clamped between the said outer part of the key member and the said projecting surface, and the said inner and further parts of the key member being snap-fastened together.

7. A keyboard according to claim 1, wherein the said outer part of the key member is substantially square-shaped and is provided with a central circular-shaped cover matching with finger contour and, in a corner thereof, with a transparent window for a signal-lamp.

8. A keyboard according to claim 1, wherein the said deformable diaphragm further has a pre-cut line reducing thickness thereof, said line forming the contour of an opening having the same shape and substantially the same dimensions as a key member.

9. A keyboard according to claim 8, wherein that transparent cap for a signal lamp is fitted in the said opening of the diaphragm.

* * * * *

UNITED STATES PATENT AND TRADEMARK OFFICE

CERTIFICATE OF CORRECTION

PATENT NO. : 4,471,189

DATED : September 11, 1984

INVENTOR(S) : Bacon et al.

It is certified that error appears in the above-identified patent and that said Letters Patent are hereby corrected as shown below:

On the title page

-- (75) Inventors: Remy Bacon, Dignac; Gerard Juery, Ruelle; and Michel Naulin, Angouleme, all of France --

Signed and Sealed this

*Twenty-sixth* Day of *March 1985*

[SEAL]

*Attest:*

DONALD J. QUIGG

*Attesting Officer* *Acting Commissioner of Patents and Trademarks*